(12) United States Patent
Lim

(10) Patent No.: US 7,081,359 B2
(45) Date of Patent: Jul. 25, 2006

(54) **RECOMBINANT *BACILLUS* PROTEASES AND USES THEREOF**

(75) Inventor: Boon Leong Lim, Pokfulam (HK)

(73) Assignee: Enzymes Technology Limited, Kwai Chung (HK)

( * ) Notice: Subject to any disclaimer, the term of this patent is extended or adjusted under 35 U.S.C. 154(b) by 292 days.

(21) Appl. No.: 10/146,905

(22) Filed: May 17, 2002

(65) Prior Publication Data

US 2003/0215906 A1    Nov. 20, 2003

(51) Int. Cl.
*C12P 21/06* (2006.01)
*C12N 9/50* (2006.01)
*C12N 9/54* (2006.01)
*C12N 15/00* (2006.01)
*C07H 21/04* (2006.01)

(52) U.S. Cl. .................. 435/219; 435/69.1; 435/221; 435/222; 435/320.1; 435/252.31; 536/24.1; 536/23.2

(58) Field of Classification Search ............. 435/320.1, 435/69.1, 220, 252.31, 221, 222, 219; 536/24.1, 536/23.2
See application file for complete search history.

(56) References Cited

OTHER PUBLICATIONS

Jacobs MF. Expression of the subtilisin Carlsberg-encoding gene in *Bacillus licheniformis* and *Bacillus subtilis*. Gene. Jan. 11, 1995;152(1):69-74.

Jacobs et al. Cloning, sequencing and expression of subtilisin Carlsberg from *Bacillus licheniformis*. Nucleic Acids Res. Dec. 20, 1985;13(24):8913-26.

Leung and Errington, Characterization of an insertion in the phage phi 105 genome that blocks host *Bacillus subtilis* lysis and provides strong expression of heterologous genes. Gene. Feb 27, 1995;154(1):1-6.

Thornewell et al. An efficient expression and secretion system based on *Bacillus subtilis* phage phi 105 and its use for the production of *B. cereus* beta-lactamase I. Gene, Oct. 29, 1993;133(1):47-53.

van der Laan et al. Cloning, characterization, and multiple chromosomal integration of a *Bacillus* alkaline protease gene. Appl Environ Microbiol. Apr. 1991;57(4):901-9.

Wells et al. Cloning, sequencing, and secretion of *Bacillus amyloliquefaciens* subtilisin in *Bacillus subtilis*. Nucleic Acids Res. Nov. 25, 1983;11(22):7911-25.

Zaghloul et al. High level of expression and stability of the cloned alkaline protease (aprA) gene in *Bacillus subtilis*. Enzyme Microb Technol. Jun. 1994;16(6):534-7.

*Primary Examiner*—Rebecca E. Prouty
*Assistant Examiner*—Malgorzata Walicka
(74) *Attorney, Agent, or Firm*—Dickstein Shapiro Morin & Oshinsky LLP

(57) ABSTRACT

The present invention provides genetically engineered *Bacillus* strains that can secrete large amount of *Bacillus* proteases in the extracellular culture medium. More particularly, this invention relates to a process of producing recombinant protease molecules of *Bacillus* origin in a *Bacillus subtilis* strain 168, utilizing a strong prophage promoter.

6 Claims, 6 Drawing Sheets

Figures 1A, 1B:
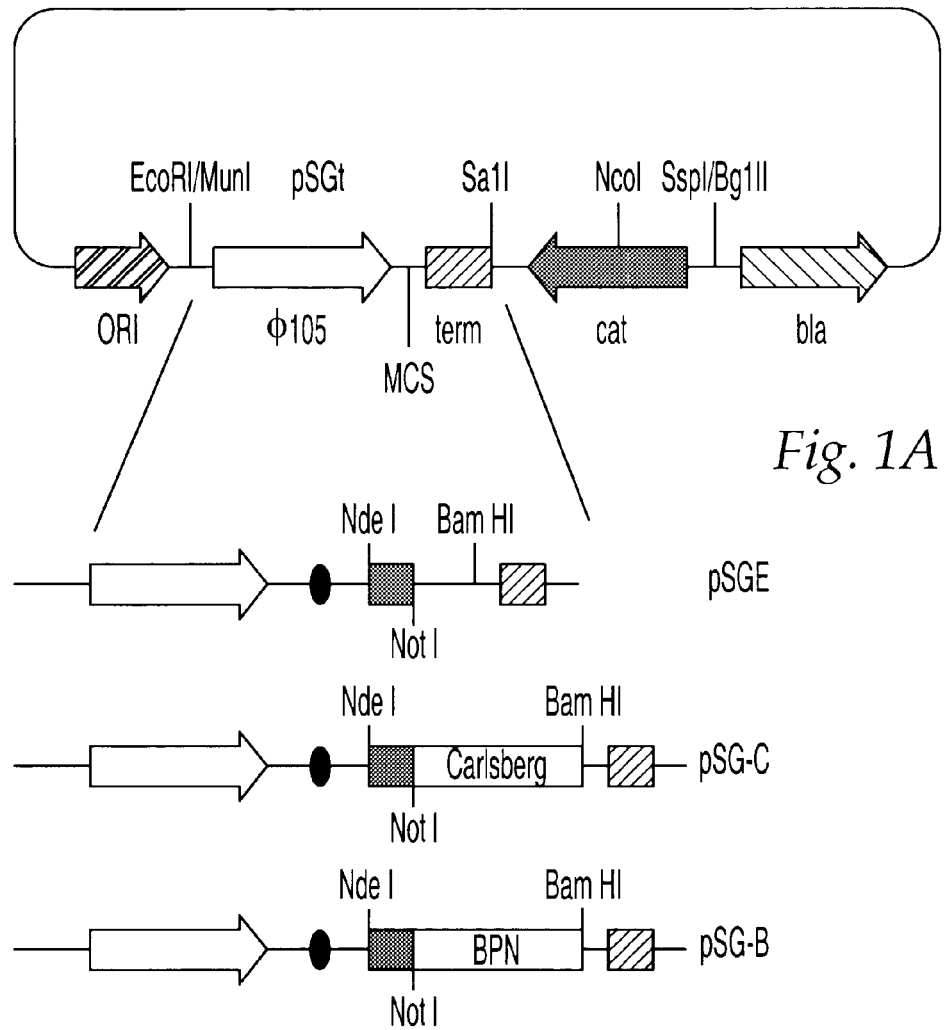

```
Carlsberg [SEQ ID NO:12]   1 MRSKKLWISL LFALTLIFTM AFSNMSAQAA -AQPAKNVEK DYIVGFKSGV    50
BPN       [SEQ ID NO:11]   1 MRSKKLWISL LFALTLIFTM AFSNMSAQAA AGKSNGEKKY IVGFKQTMST    50

Carlsberg                 51 KTASVKKDII KESGGKVDKQ FRIINAAKAK LDKEALKEVK NDPDVAYVEE   100
BPN                       51 MSAAKKKDVI SEKGGKVQKQ FKYVDAASAT LNEKAVKELK KDPSVAYVEE   100

Carlsberg                101 DHVAHALAQT VPYGIPLIKA DKVQAQGFKG ANVKVAVLDT GIQASHPDLN   150
BPN                      101 DHVAHAYAQS VPYGVSQIKA PALHSQGYTG SNVKVAVIDS GIDSSHPDLK   150

Carlsberg                151 VVGGASFVAG EAINTNDGNG HGTHVAGTVA ALDNTTGVLG VAPSVSLYAV   200
BPN                      151 VAGGASMVPS ETNPFQDNNS HGTHVAGTVA ALNNSIGVLG VAPSASLYAV   200

Carlsberg                201 KVLNSSGSGT YSGIVSGIEW ATTNGMDVIN MSLGGPSGST AMKQAVDNAY   250
BPN                      201 KVLGADGSGQ YSWIINGIEW AIANNMDVIN MSLGGPSGSA ALKAAVDKAV   250

Carlsberg                251 ARGVVVVAAA GNRGSSGNTE TIGYPAKYDS VIAVGAVDSN SNRASFSSVG   300
BPN                      251 ASGVVVVAAA GNEGTSGSSS TVGYPGKYPS VIAVGAVDSS NQRASFSSVG   300

Carlsberg                301 AELEVMAPGA GVYSTYPTST YATLNGTSMA SPHVAGAAAL ILSKHPNLSA   350
BPN                      301 PELDVMAPGV SIQSTLPGNK YGAYNGTSMA SPHVAGAAAL ILSKHPNWTN   350

Carlsberg                351 SQVRNRLSST ATYLGSSFYY GKGLINVEAA AQ*.......                400
BPN                      351 TQVRSSLENT TTKLGDSFYY GKGLINVQAA AQ*.......                400
```

Fig. 2

RECOMBINANT *BACILLUS* PROTEASES AND USES THEREOF

FIELD OF THE INVENTION

In this invention, a rapid expression system for *Bacillus* proteases was established. Genetically engineered *Bacillus* strains that can secrete large amount of *Bacillus* proteases in the extracellular culture medium were generated. More particularly, this invention relates to a process of producing recombinant protease molecules of *Bacillus* origin in a *Bacillus subtilis* strain 168, utilizing a strong prophage promoter.

BACKGROUND OF INVENTION

Subtilisin enzymes usually refer to extracellular serine endopeptidases from related *Bacillus* species: for example subtilisin Carlsberg from *Bacillus licheniformis* (Jacobs et al., Nucleic Acids Res 13: 8913–8926, 1985); subtilisin BPN from *Bacillus amyloliquifaciens* (Wells et al., Nucleic Acids Res 11: 7911–7925, 1983) and alkaline protease PB92 from *Bacillus alcalophilus* PB92 (Van Der Laan et al., Appl. Environ. Microbiol. 57, 901–909, 1991) etc. Subtilsin enzymes have been studied extensively in last decades because of their usefulness as additives to detergents, esp. to laundry detergents.

There are several advantages about these subtilisins mentioned above. They usually possess high efficiency and little specificity e.g. they can degrade almost all kinds of proteins. They can exhibit activity at high pH (pH 8–12) and in the presence of some surfactants. In addition they are extracellular enzymes secreted by the bacteria into the medium. Thus they can be isolated without breaking the bacterial cells, which makes the purification process easier and less costly.

To be suitable for use in detergents, proteases must exhibit the following properties:
1. They must possess broad substrate specificity;
2. They must have activity and stability at alkaline pH range.
3. They must be stable at high temperature and in the presence of chelating agents, perborates and surfactants.
4. They must be efficacious at low temperatures (20–40° C.).

However, the yield of subtilisin naturally secreted by *Bacillus* species is usually low and could not meet the requirement of industry. Fortunately, the application of genetic engineering has greatly enhanced its production yield (Jacobs et al., Gene 152: 69–74, 1995; Zaghloul et al., Enzyme Microb Technol 16: 534–537, 1994). Now subtilisins can be industrially produced. In this patent an expression system based on *Bacillus subtilis* was successfully used to produce subtilisins with high yield in a short period of time.

Enzyme Production by the Phase φ105 Overexpression System

In a previously established φ105 system (Thornewell et al., Gene 133:47–53, 1993), a defective prophage vector, φ105MU331 was derived for high-level protein over-expression expression in *B. subtilis* (Leung & Errington, Gene 154(1):1–6, 1995). In this derived system, not only efficient inducible (by heat) transcription of the gene is provided, but also, it prevented the lysis of the host cell. Thus the enzyme produced can be collected easily in the culture media without disruption of the cells, which means the purification steps can be greatly diminished. In addition to this, unlike *E. coli*, Bacilli are GRAS bacteria, the genes encoding their proteins are also GRAS to animals and thus, human.

SUMMARY OF THE INVENTION

The present invention provides genetically engineered *Bacillus* strains that can secrete large amount of *Bacillus* proteases in the extracellular culture medium. More particularly, this invention relates to a process of producing recombinant protease molecules of *Bacillus* origin in a *Bacillus subtilis* strain 168, utilizing a strong prophage promoter and a signal peptide from subtilisin E of the *Bacillus subtilis*.

Preferred molecules of the present invention include protease genens subtilisin Carlsberg (SEQ ID NO:9), and subtilisin BPN' (SEQ ID NO:7) from *Bacillus licheniformis* (ATCC 10716) and *Bacillus amyloliquifaciens* (ATCC 23844), respectively.

It is another object of the present invention to provide a rapid process for producing large quantity of protease enzyme.

In accordance with one aspect of the present invention, there are provided protease enzymes for applications in commercial processes, such as, detergent applications.

In a further aspect of the present invention, there is provided a process for producing related proteases by recombinant technology comprising a *Bacillus* host and the strong prophage promoter described in this invention.

In this invention, an integration vector pSGE containine the DNA of the signal peptide (SEQ ID NO:15) of the subtilisin E gene from a *Bacillus subtilis* strain was constructed. Subtilisin E is a natural secretion protein of *Bacillus subtilis*. In our studies, the expression yields of the proteases subtilisin Carlsberg and subtilisin BPN' cloned from *Bacillus licheniformis*;(ATCC 10716) and *Bacillus amyloliquifaciens* (ATCC 23844) were greatly enhanced by replacing the native signal peptides of these proteases with that of the Subtilisin E. Since both target proteases were heterologous proteins to *Bacillus subtilis,* their signal peptides could not be properly processed by the secretory machinery of *B. subtilis*. By exchanging their signal peptides with that of the subtilisin E, this allowed proper secretion of these proteins.

The signal peptide DNA sequence from subtilisin E gene was first amplified by PCR and then cloned into the plasmid pSGt, which contains a terminator DNA from the α-amylase gene of *Bacillus licheniformis*. The plasmid containing signal peptide sequence of subtilisin E gene and terminator sequence of α-amylase gene was designated pSGE (FIG. 1).

Two alkaline protease genes, including subtilisin Carlsberg (SEQ ID NO:9) from *Bacilus licheniformis* (ATCC 10716) and subtilisin BPN' (SEQ ID NO:7) from *Bacillus amyloliquifaciens* (ATCC 23844), were amplified and cloned into the integration vector pSGE, to create pSG-C and pSG-B, respectively. Plasmids containing these protease genes were then transformed into *B. subtilis*. Then transformants were screened on milk plate. Some transformants that showed larger clear zones than negative control on milk plate were used to overproduce the target proteases.

The invention features nucleic acid molecules which are at least 45% (or 55%, 65%, 75%, 85%, 95%, 98% or 99%) identical to the nueleotide sequence of any of SEQ ID NOS:7, 9, 14, or a complement thereof.

The invention features nucleic acid molecules which are at least 45% (or 55%, 65%, 75%, 85%, 95%, or 98%) identical to the nucleotide sequence of any of SEQ ID 7, 9, or a complement thereof, wherein such nucleic acid molecules encode polypeptides or proteins that exhibit at least one structural and/or functional feature of a polypeptide of the invention.

The invention features nucleic acid molecules of at least 200, 250, 300, 350, 400, 450, 500, 550, 575, 600, 625, 650, 675, 700, 725, 750, 800, 850, 900, 950, 1000, 1050, 1100, 1125 or 1149 nucleotides of the nucleotide sequence of SEQ ID NO: 7.

The invention features nucleic acid molecules which include a fragment of at least least 200, 250, 300, 350, 400, 450, 500, 550, 575, 600, 625, 650, 675, 700, 725, 750, 800, 850, 900, 950, 1000, 1050, 1100, 1125 or 1140 nucleotides of the nucleotide sequence of SEQ ID NO:9, or a complement thereof.

The invention features nucleic acid molecules of at least 250, 275, 300, 325, 350, 375, 400, 425, 450, or 479 nucleotides of the nucleotide sequence of SEQ ID NO:14, or a complement thereof.

The invention also features nucleic acid molecules which include a nucleotide sequence encoding a protein having an amino acid sequence that is at least 45% (or 55%, 65%, 75%, 85%, 95%, 98%, or 99%) identical to the amino acid sequence of any of SEQ ID Nos:8, 10, 11, or 12.

The invention also features nucleic acid molecules which include a nucleotide sequence encoding a protein having an amino acid sequence that is at least 45% (or 55%, 65%, 75%, 85%, 95%, 98%, or 99%) identical to the amino acid sequence of any of SEQ ID Nos:8, 10, 11, or 12, wherein the protein encoded by the nucleotide sequence also exhibits at least one structural and/or functional feature of a polypeptide of the invention.

Also within the invention are nucleic acid molecules which encode a fragment of a polypeptide having the amino acid sequence of any of SEQ ID Nos: 8, 10, 11, or 12, the fragment including at least 15 (20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 381 or 382) contiguous amino acids of any of SEQ ID NOs:8, 10, 11, or 12.

Also within the invention are nucleic acid molecules which encode a fragment of a polypeptide having the amino acid sequence of any of SEQ ID Nos: 8, 10, 11, or 12, the fragment including at least 15 (20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 381 or 382) contiguous amino acids of any of SEQ ID NOs:8, 10, 11, or 12, wherein the fragment exhibits at least one structural and/or functional feature of a polypeptide of the invention.

The invention includes nucleic acid molecules which encode a naturally occurring allelic variant of a polypeptide comprising the amino acid sequence of any of SEQ ID Nos: 8, 10, 11, or 12, wherein the nucleic acid molecule hybridizes under stringent conditions to a nucleic acid molecule having a nucleic acid sequence encoding any of SEQ ID Nos:8, 10, 11, or 12, or a complement thereof.

The invention includes nucleic acid molecules which encode a naturally occurring allelic variant of a polypeptide comprising the amino acid sequence of any of SEQ ID Nos:8, 10, 11, or 12, wherein the nucleic acid molecule hybridizes under stringent conditions to a nucleic acid molecule having a nucleic acid sequence encoding any of SEQ ID Nos:8, 10, 11, or 12, or a complement thereof, wherein such nucleic acid molecules encode polypeptides or proteins that exhibit at least one structural and/or functional feature of a polypeptide of the invention.

Also within the invention are isolated polypeptides or proteins having an amino acid sequence that is at least about 65%, preferably 75%, 85%, 95%, 98%, or 99% identical to the amino acid sequence of any of SEQ ID Nos:8, 10, 11, or 12.

Also within the invention are isolated polypeptides or proteins having an amino acid sequence that is at least about 65%, preferably 75%, 85%, 95%, or 98% identical to the amino acid sequence of any of SEQ ID Nos:8, 10, 11, or 12, wherein the polypeptides or proteins also exhibit at least one structural and/or functional feature of a polypeptide of the invention.

Also within the invention are polypeptides which are naturally occurring allelic variants of a polypeptide that includes the amino acid sequence of any of SEQ ID Nos:8, 10, 11, or 12, wherein the polypeptide is encoded by a nucleic acid molecule which hybridizes under stringent conditions to a nucleic acid molecule having the sequence of any of SEQ ID Nos:7, 9, or a complement thereof.

Also within the invention are polypeptides which are naturally occurring allelic variants of a polypeptide that includes the amino acid sequence of any of SEQ ID Nos:8, 10, 11, or 12, wherein the polypeptide is encoded by a nucleic acid molecule which hybridizes under stringent conditions to a nucleic acid molecule having the sequence of any of SEQ ID Nos:7 or 9, or a complement thereof, wherein such nucleic acid molecules encode polypeptides or proteins that exhibit at least one structural and/or functional feature of a polypeptide of the invention.

In yet another embodiment, a method is provided for producing a polypeptide, comprising:
 (a) cultivating a *Bacillus* cell in a medium conducive for the production of a polypeptide, wherein the *Bacillus* cell comprises a nucleic acid construct comprising a Φ105MU331 promoter in which the Φ105MU331 promoter sequence is operably linked to a nucleic acid sequence encoding the polypeptide; and
 (b) isolating the polypeptide from the cultivation medium.

In yet another embodiment of the above recited method, the nucleic acid sequence encodes a protease subtilisin gene product, Carlsberg (SEQ ID NO:10), cloned from a *Bacillus licheniformis* strain (ATCC No. 10716), the protease subtilisin BPN' gene product (SEQ ID NO:8) from *Bacillus amyloliquifaciens* (ATCC No. 23844), or a combination thereof.

In yet another embodiment of the above recited method, the nucleic acid sequence encodes a protease subtilisin gene product coding sequence, Carlsberg (SEQ ID NO:9), cloned from a *Bacillus licheniformis* strain (ATCC No. 10716), the protease subtilisin BPN' gene (SEQ ID NO:7) from *Bacillus amyloliquifaciens* (ATCC No. 23844), or a combination thereof.

In yet another embodiment of the above recited method, the nucleic acid sequence encodes a protease subtilisin gene product coding sequence, Carlsberg (SEQ ID NO:9), cloned from a *Bacillus licheniformis* strain (ATCC No. 10716), or the protease subtilisin BPN' gene (SEQ ID NO:7) from *Bacillus amyloliquifaciens* (ATCC No. 23844) operably linked to the 30 amino acid signal peptide (SEQ ID NO:15) of *Bacillus subtilis* 168 subtilisin E.

In yet another embodiment of the above recited method, the nucleic acid construct further comprises a selectable marker gene.

In yet another embodiment of the above recited method, the selectable marker is the CAT gene.

In yet another embodiment of the above recited method, the Bacillus cell contains no selectable marker gene.

In yet another embodiment of the above recited method, the nucleic acid sequence encodes a polypeptide heterologous to the Bacillus cell.

In yet another embodiment of the above recited method, the polypeptide is a hormone or variant thereof, enzyme, receptor or portion thereof, antibody or portion thereof, or reporter.

In yet another embodiment of the above recited method, the enzyme is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

In yet another embodiment of the above recited method, the Bacillus host cell is a Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis, Bacillus thuringiensis, Bacillus thermoleovorans strain (ATCC No. 43506), Bacillus subtilis strain 168, or Bacillus subtilis strain MU331.

In yet another embodiment of the above recited method, the nucleic acid sequence encodes a polypeptide homologous to the Bacillus cell.

In yet another embodiment of the above recited method, the polypeptide is a protease.

In yet another embodiment of the above recited method, the Bacillus cell is a Bacillus amyloliquefaciens cell.

In yet another embodiment of the above recited method, the Bacillus cell is a Bacillus licheniformis cell.

FIGURE LEGENDS

The following figures illustrate the embodiments of the invention and are not meant to limit the scope of the invention encompassed by the claims.

FIG. 1. (A) Schematic map of the expression vector pSGt. Heterologous gene(s) is inserted into the multicloning sites (MCS) of the vector. The vector carries a pBR 322 replication origin ORI for E. coli, the promoter and the ribosome binding site of the ORF 19 of the bacteriophage phi-105 (Φ-105), the terminator of B. licheniformis α-amylase (term), a cat gene for chloramphenical resistance and a bla gene for ampicillin resistance. (B) Schematic maps of the expression vectors pSG-E, pSG-C and pSG-B.

FIG. 2. The amino acid sequences of the subtilisin E-protease fusion proteins. Amino acid residues representing the signal peptide of B. subtilis subtilisin E were shown in Italics. The DNA sequences encoding the mature proteases subtilisin Carlsberg and subtilisin BPN' were cloned in frame with the signal peptide of B. subtilis subtilisin E. The amino acid residues determined by N-terminal protein sequencing were underlined.

Figure 3A:
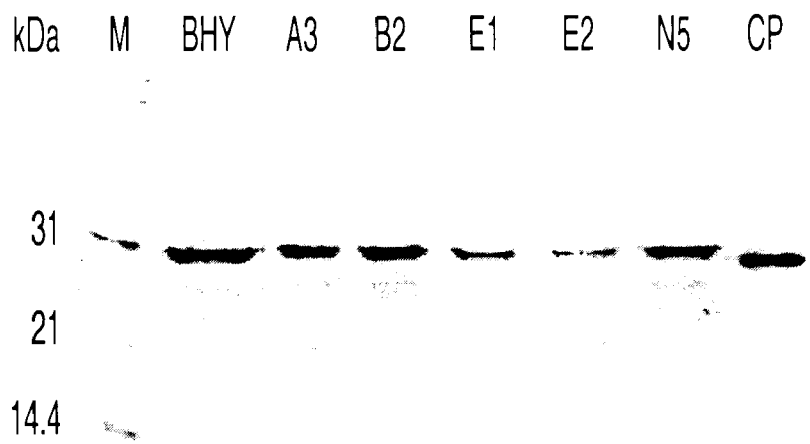
Figure 3B:
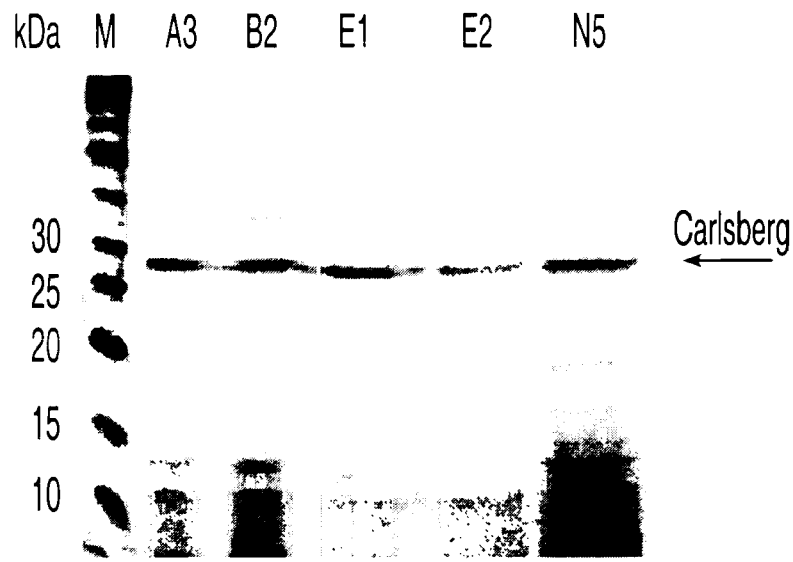

FIG. 3. Overexpression of the recombinant proteases in shaking flasks using various media. (A) Overexpression of protease BPN'. (B) Overexpression of protease Carlsberg. At 4 hours after heat induction, 10 ul culture supernatants were run into each lane. Protein markers were loaded on the first lane on the left. CP: 100 ug commercial enzyme powder concentrate from NovoNordis (Savinase 4.0T).

Figure 4A:
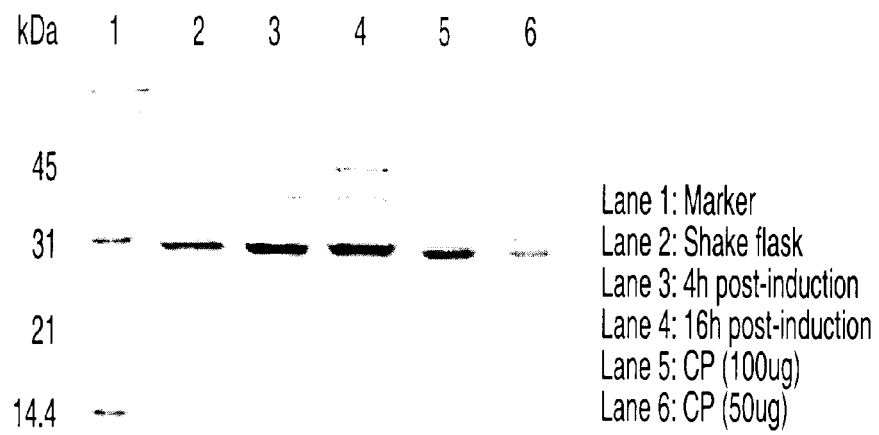
Figure 4B:
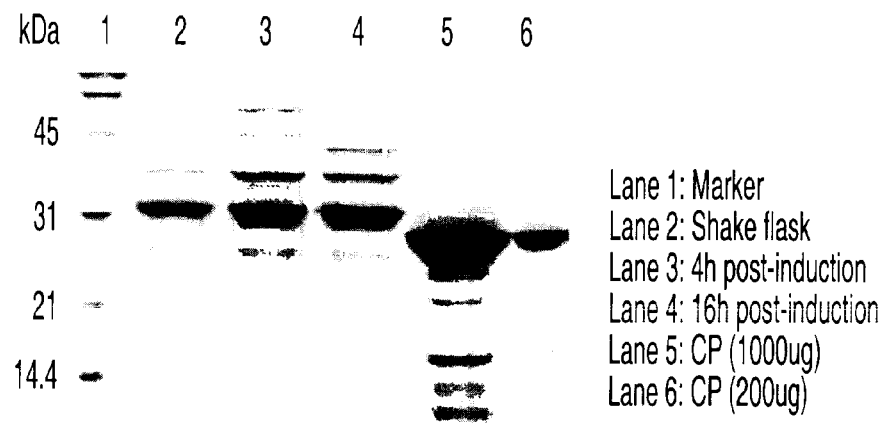

FIG. 4. Overexpression of the recombinant proteases in a 2 L fermentor. (A) Overexpression of protease BPN'. (B) Overexpression of protease Carlsberg. Protein markers were loaded on the first lane on the left. CP: 100 ug commercial enzyme powder concentrate from NovoNordis (Savinase 4.0T).

Figure 5:
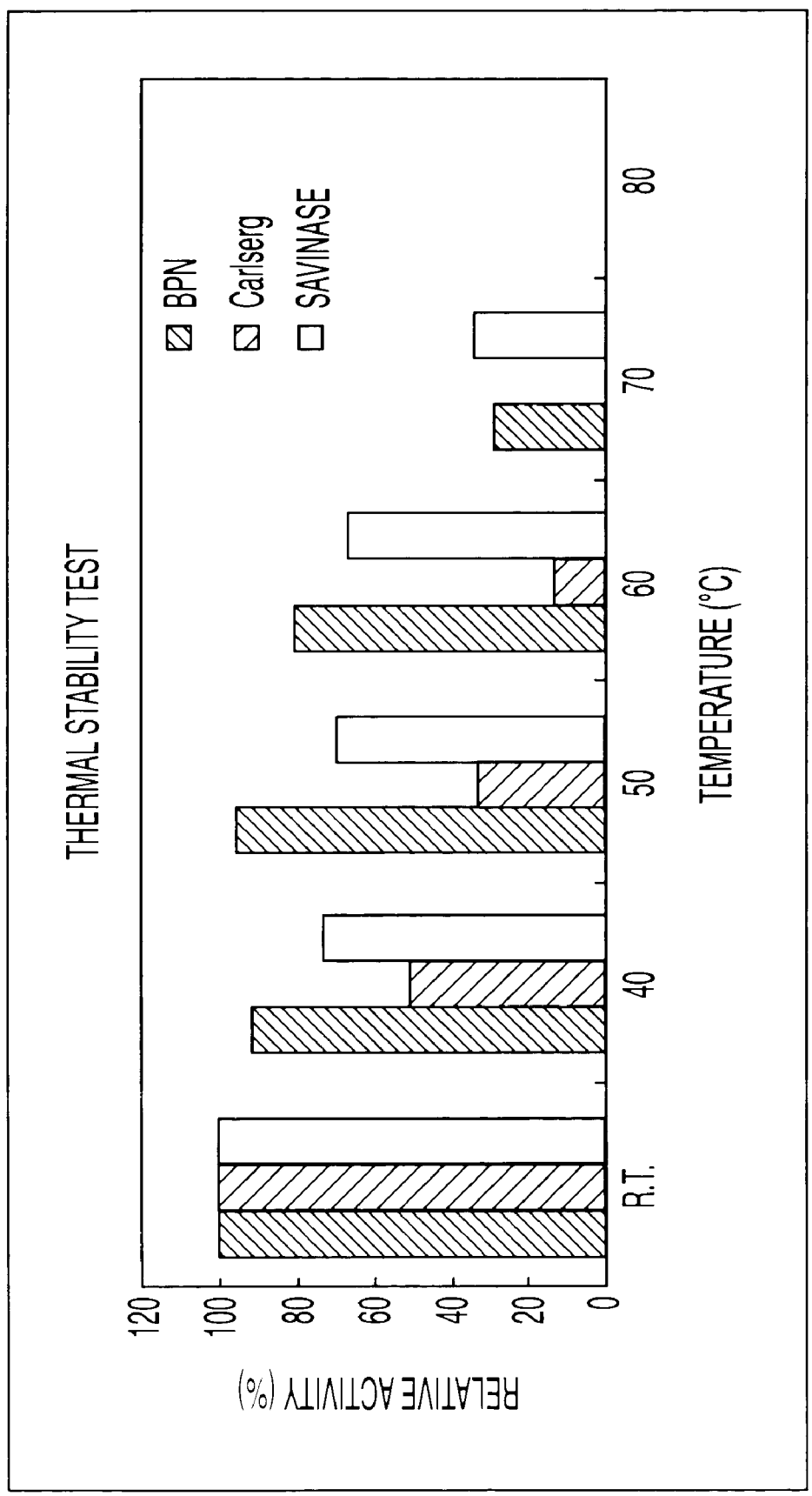

FIG. 5. Thermal stability test.

Figure 6:
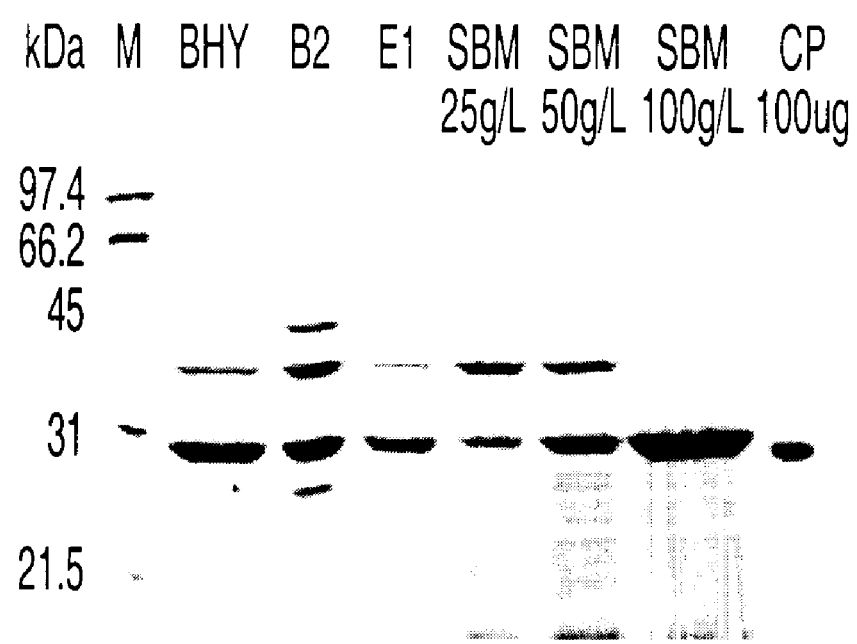

FIG. 6. Overexpression of protease BPN' using a medium rich in soybean meal (SBM). 10 µl supernatants were run into each lane. CP: 100 ug commercial enzyme powder concentrate from NovoNordis (Savinase 4.0T).

EXAMPLES

1. Amplication of Protease Genes from B. subtilis Strain 168, Bacillus amyloliquifaciens and Bacillus licheniformis Bacillus subtilis 168, Bacillus amyloliquifaciens (ATCC 23844) and Bacillus licheniformis (ATCC 10716) were used as the source of chromosomal DNA. PCR was performed with three pairs of primer (Table 1). The first pair of primer, SubES (SEQ. ID No. 1) and SubEA (SEQ. ID No. 2) was used to amplify the signal peptide of the subtilisin E gene from Bacillus subtilis 168. The other two pairs of primers, BPN'-S (SEQ. ID No. 3)/BPN'-A (SEQ. ID No. 4) and CAR-S (SEQ. ID No. 5)/CAR-A(SEQ. ID No. 6) were used to amplify the protease genes BPN' and Carlsberg from B. licheniformis and B. amyloliquifaciens, respectively. PCR was carried out for 30 cycles with each cycle composed of 4 min at 94° C. (denaturation), 40 second at 53° C. (annealing), 3 min at 75° C. (extension), Pfu polymerase was employed to safeguard the fidelity of the reaction. The DNA and its deduced amino acid sequences of protease BPN' are shown in SEQ. ID No. 7 and SEQ. ID No. 8, whereas those of the protease Carlsberg are shown in SEQ. ID No. 9 and SEQ. ID No. 10. It was expected that the signal peptides of the proteases from B. licheniformis and B. amyloliquifaciens might not be correctly processed in the expression host B. subtilis, therefore only the gene fragment encoding for the mature enzyme was amplified.

TABLE 1

Primers employed in this study

| Primer name | Sequence | Orientation | Template |
|---|---|---|---|
| SubES (SEQ ID NO:1) | gcgatcg<u>CATATG</u>AGAAGCAAAAAATTGTGGATCAGC | sense | Signal peptide for subtilisin E |
| SubEA (SEQ ID NO:2) | gcggatcc<u>GCGGCCGC</u>CTGCGCAGACATGTTGC | antisense | Signal peptide for subtilisin E |

TABLE 1-continued

Primers employed in this study

| Primer name | Sequence | Orientation | Template |
|---|---|---|---|
| BPN-S (SEQ ID NO:3) | gcgatatcGCGGCCGCAGGGAAATCAAACGGGGAA | sense | Mature BPN gene |
| BPN-A (SEQ ID NO:4) | gcGGATCCACTTGGCCGTTACGGGACT | antisense | Mature BPN gene |
| CAL-S (SEQ ID NO:5) | gcgatatcGCGGCCGCTCAACCGGCGAAAAATGTT | sense | Mature Calsberg gene |
| CAL-A (SEQ ID NO:6) | gcGGATCCTTATTGAGCGGCAGCTTCGAC | antisense | Mature Calsberg gene |
| phi-1-5 SEQ ID NO:13) | ATAGACAATCGGCGGTTAAC | sense | phi-105 ORF19 promoter |

2. Construction of pSGt Expression Plasmids Carrying the Protease Genes

The PCR fragments were purified by phenol/chloroform extraction and ethanol precipitation. The DNA fragment obtained by the SubE primers, the BPN' primers and the CAR primers were subjected to Nde I/Bam H1, Not I/Bam HI and Not I/Bam HI restriction enzyme digestion, respectively. Since Subtilisin E is of B. subtilis origin, its native signal peptide was compatible to the expression host strain B. subtilis. Therefore, the coding sequence of its signal peptide was subcloned into the Nde I and Bam HI sites of the cloning vector pSGt (FIG. 1) to create pSG-E, in which a Not I site was engineered. On the other hand, since the signal peptides of the protease from B. licheniformis and B. amyloliquifaciens were not compatible to B. subtilis, only the coding sequences of the mature enzymes were cloned into the NotI/BamHI sites of the pSGE to create pSG-B and pSG-C. The map of these vectors is shown in FIG. 1B. The amino acid sequences of the resultant fusion proteins (SEQ. ID Nos. 11 and 12) were aligned in FIG. 2. After ligation overnight, the plasmids were ethanol precipitated before transformation into E. coli. Competent E. coli cells (Top 10) were prepared and transformed by electroporation with the Bio Rad pulser under the conditions recommended by the supplier. The electroporated cells were transferred to 2×YT and incubated at 37° C. for 40 minutes before spreading onto LB-agar plates with ampicillin (100 µg/ml). After overnight incubation, colonies were picked from the LA-agar plates and screened by PCR. Positive clones were selected and grown in LB broth with ampicillin (100 µg/ml) overnight. The plasmids were extracted from the cells by using the Bio Rad Quantum prep Plasmid Miniprep kit, under the recommended conditions.

3. Transformation of Bacillus subtilis

A Bacillus recipient strain (B. subtilis MU331) was streaked onto a LB-agar plate with erythromycin (5 µg/ml) and incubated at 37° C. overnight. Multiple colonies were inoculated into 5 ml pretransformation medium [(PTM)—2.2% (v/v) of 40% w/v glucose; 1% (v/v) solution P (0.5 ml of 0.1M CaCl$_2$.2H$_2$O, 2.5 ml of 1.0M MgSO$_4$.7H$_2$O, 0.01 ml of 1.0M MnSO$_4$.4H$_2$O and 7.0 ml ddH$_2$O); 1.8% (v/v) Casamino (2 g/L); 1% (v/v) Tryptophan (2 mg/ml); 1% (v/v) Isoleucine (20 mg/ml); 1% (v/v) Valine (20 mg/ml); 1% (v/v) Leucine (20 mg/ml); 1% (v/v) Methionine (5 mg/ml); 90% (v/v) of Spizizen minimal medium (0.2% (w/v) ammonium sulphate, 1.4% (w/v) dipotassium phosphate, 0.6% (w/v) potassium dihydrogen phosphate, 0.1% (w/v) sodium citrate dihydrate, 0.02% (w/v) magnesium sulphate)], and incubated at 37° C. with shaking at 280 rpm. Cell growth was monitored, until OD$_{600}$ reached 3.0~3.3.

One-hundred (100) µl of competent cells were mixed with about 2 µg DNA and transferred into 1 ml pre-warmed (37° C.) transformation medium[(TM)—1.4% (v/v) of 40% (w/v) glucose; 0.47% (v/v) solution F (1.0M MgSO$_4$.7H$_2$O); 0.05% (v/v) Casamino (2 g/l); 0.93% (v/v) Tryptophan (2 mg/ml); 0.93% (v/v) Isoleucine (20 mg/ml); 0.93% (v/v) Valine (20 mg/ml); 0.93% (v/v) Leucine (20 mg/ml); 0.93% (v/v) Methionine (5 mg/ml); 93.4% (v/v) of Spizizen minimal medium (0.2% (w/v) ammonium sulphate, 1.4% (w/v) dipotassium phosphate, 0.6% (w/v) potassium dihydrogen phosphate, 0.1% (w/v) sodium citrate dihydrate, 0.02% (w/v)magnesium sulphate)] and incubated at 37° C. with shaking at 280 rpm for 1.5 hour. The culture was centrifuged (13,200 rpm, 2 min) and 150 µl was spread onto LB-agar plates with chloramphenicol (5 µg/ml). The plates were incubated at 37° C. overnight and each single colony was transferred onto a LB-agar plate with erythromycin (5 µg/ml) and one with chloramphenicol (5 µg/ml) on the next day. PCR screening was performed on the colonies by using a promoter specific primer, phi-105, (SEQ ID NO:13) and one of the protease specific antisense primers.

4. Overexpression of Proteases in B. subtilis MU331

Bacterial cells from frozen stock was streaked onto LB-agar plate with chloramphenicol (5 µg/ml) and incubated at 37° C. overnight. A single colony was inoculated into 15 ml BHY medium (3.7% (w/v) brain-heart infusion broth, 0.5% (w/v) yeast extract) with chloramphenicol (5 µg/ml) and incubated at 37° C. with shaking at 270 rpm overnight. 12 ml of the overnight culture was transferred into 100 ml BHY medium without chloramphenicol, and incubated at 37° C. with shaking at 280 rpm. Cell growth was monitored by reading OD$_{600}$ until it reached 5.3–5.9. Heat shock was then performed by placing the sample in a 50° C. water-bath for 8 minutes with vigorous shaking and then re-incubated at 37° C., with shaking at 280 rpm. At 4 hours post-induction, all samples were collected and centrifuged to remove cell pellets.

5. N-terminal Amino Acid Sequence Analysis

N-terminal amino acid sequence analysis was performed after protein separation by SDS/PAGE and transferred to PVDF membrane. The band of interest was cut out and subjected to automated Edman degradation with the Hewlett Packard protein sequencer (model G1000A), in accordance with the manufacturer's instruction. Analysis of the N-terminal sequence of the mature protease A shows that the signal peptides and the propeptides of the proteases were correctly cleaved. The first seven amino acid residues of the mature protease Carlsberg and BPN' were AQTVPYG and AQSVPYG, respectively. As a result, both mature proteases had 275 amino acid residues.

6. Protease Activity Assay Using succinyl-Ala-Ala-Pro-Phe-p-nitroanilide (SucAAPF-pNA) Mitchinson and Wells, Biochemistry 28: 4807–4815, 1989)

A synthetic substrate succinyl-Ala-Ala-Pro-Phe-p-nitroanilide (SucAAPF-pNA) was employed for protease activity enzyme. The colourless substrate can be converted into a yellowish product, p-nitroanilide (pNA), by protease activity. A 0.5 mM stock of SucAAPF-pNA was prepared in a 0.1 M Tris-HCl buffer, pH 8.6 and the enzyme-containing culture supernatants were diluted in the same buffer. 10 ul diluted enzyme was then mixed with 190 ul substrate in triplicate into the wells of a 96 well ELISA plate and incubated at 22° C. A blank was prepared by mixing 10 ul Tris-HCl buffer with 190 ul substrate. OD reading at 405 nm was taken at 20 mins and 30 mins, respectively. To prepare a standard curve, a 1 mM p-nitroaniline (pNA) stock was serially diluted and $OD_{405}$ readings were measured. One enzyme unit (EU) is defined as the amount of enzyme that releases 1 micromole of pNA per minute at 22° C.

7. Protease Activity Assay Using Azocoll as Substrates (Chavira, et al., Anal Biochem 136: 446–450 1984)

50 mM Tris-HCl containing 5 mM calcium chloride at pH 8.0 was used as the assay buffer. 150 mg Azocoll was first stirred in 30 ml of assay buffer for 2 hours before filtered through a Whatmnan No. 1 filter paper to remove the filtrate. The undissolved pellet was resuspended in 30 ml assay buffer and 1 ml aliquots were made. Protease in the culture supernatant was diluted 50 times in the assay buffer and 20 ul diluted enzyme is added to 1 ml Azocoll suspension which has been preheated at 37° C. After incubating the mixture at 37° C. for 1 hour, the reaction was stopped on ice bath and unhydrolysed azocoll was removed by centrifugation at 10000 g for 5 min. The color of the supernatant was measured at $OD_{520}$nm. One enzyme unit (EU) is defined as the amount of enzyme that produces an $OD_{520}$ nm of 0.5.

8. Overexpression of the Proteases in Shake Flasks Using Industrial Media

Five media were formulated by industrial grade chemicals and their ability to support protease overexpression was examined. The formulations are shown in Table 2. A single colony was inoculated into 15 ml BHY medium (3.7% (w/v) brain-heart infision broth, 0.5% (w/v) yeast extract) with chloramphenicol (5 μg/ml) and incubated at 37° C. with shaking at 270 rpm overnight. 1 ml of the overnight culture was transferred into 20 ml formulated media without chloramphenicol, and incubated at 37° C. with shaking at 280 rpm. Heat shock was then performed at 4 hours post-inoculation by placing the flasks in a 50° C. water-bath for 5 minutes with vigorous shaking and then re-incubated at 37° C., with shaking at 280 rpm. At 4 hours post-induction, all samples were collected and centrifuged to remove cell pellets and 20 μl supernatant collected was subjected to SDS/PAGE. The overexpression of protease Carlsberg and BPN' in various media were shown in FIGS. 3A and 3B, respectively. The enzyme activities were shown in Table 3.

TABLE 2

Formulations of various media

| Medium A3 | g/liter | Medium B2 | g/liter |
|---|---|---|---|
| Malto-dextrin | 50 | Malto-dextrin | 50 |
| $NH_4NO_3$ | 4 | $NH_4NO_3$ | 4 |
| Hydrolyzated soybean protein | 6 | Yeast extract | 10 |

| Medium E1 | g/liter | Medium E2 | g/liter |
|---|---|---|---|
| Hydrolyzated soybean protein | 25 | Hydrolyzated soybean protein | 40 |
| $CaCO_3$ | 5 | $CaCO_3$ | 5 |
| Potato Starch | 5 | Potato Starch | 5 |

| Medium N5 | g/liter | | |
|---|---|---|---|
| Glucose | 50 | | |
| $NaHCO_3$ | 5 | | |
| $(NH_4)_2HPO_4$ | 2.5 | | |
| Yeast extract | 10 | | |

TABLE 3

Enzyme activities of proteases Carlsberg and BPN' expressed in various media.

| Proteases | Substrates | BHY | A3 | B2 | E1 | E2 | N5 | CP |
|---|---|---|---|---|---|---|---|---|
| Carlsberg | sAAPF-pNA | 50.95 | 18.39 | 28.12 | 43.25 | 44.77 | 17.77 | 0.98 |
| BPN' | sAAPF-pNA | 5.70 | 3.23 | 5.26 | 2.32 | 1.41 | 3.27 | 0.98 |
| Carlsberg | Azocoll | 1176 | 404 | 604 | 950 | 985 | 391 | 180 |
| BPN' | Azocoll | 866 | 508 | 804 | 324 | 200 | 520 | 180 |

The enzyme activities are expressed in U/ml for the media BHY, A3, B2, E1, E2 and N5. For CP, a protease powder concentrate (Savinase 4.0T) from NovoNordis, the enzyme unit is expressed in U/mg.

9. Overexpression of Proteases BPN' and Carlsberg in Fermentor

A fresh *bacillus* colony was inoculated into 80 ml BHY medium with chloramphenicol and the seed culture was shaken at 37° C. at 280 rpm. After overnight incubation, 80 ml seed culture was inoculated into 1.6 L BHY medium without chloramphenicol in a 2 litre fermentor (Biostat B, B. Bruan International). The temperature was controlled at 37° C. and the pH was controlled at 7.0 by addition of acid and base. Dissolved oxygen was maintained at 30% by a control loop that varied the stir speed. Heat induction was carried out when the OD reached 5.0 by increasing the temperature to 50° C. and then decreased to 37° C. immediately. Usually this heat induction process could be completed in 30 mins. Culture supernatants were recovered at 4 hours and 16 hours post-induction for enzyme activity assay and SDS-PAGE analysis. The results of SDS-PAGE were shown in FIG. 4. In general, higher yields of proteases were obtained from fermentor than from shaking flasks.

TABLE 4

Enzyme activities of proteases Carlsberg and BPN' produced in fermentor.

| Proteases | Substrates | Shake flask | 4 hr post-induction | 16 hr post-induction | CP |
|---|---|---|---|---|---|
| Carlsberg | sAAPF-pNA | 40.1 | 81.4 | 124.39 | 0.98 |
| Carlsberg | Azocoll | 856 | 1756 | 2728 | 180 |
| BPN' | sAAPF-pNA | 2.62 | 5.32 | 6.46 | 0.98 |
| BPN' | Azocoll | 514 | 954 | 1358 | 180 |

The enzyme activities are expressed in U/ml of culture supernatant. For CP, a protease powder concentrate (Savinase 4.0T) from NovoNordis, the enzyme unit is expressed in U/mg.

10. Thermal Stability of the Proteases

The thermal stability of the expressed proteases Carlsberg and BPN' was compared with a commercial protease (Savinase 4.0T). The protease solutions were first incubated at room temperature, 40° C., 50° C., 60° C., 70° C and 80° C. for 20 min down on ice. Afterwards, the protease solutions were equilibrated to room temperature and a protease activity assay using SucAAPF-pNA as substrate was carried out. As shown in FIG. 5, the protease BPN' and the commercial protease have better thermal stability than the protease Carlsberg.

11. Overexpression of Protease BPN' Using a Medium Rich in Soybean Meal

The ability of soybean meal to support the expression of protease BPN' was investigated by the procedures described in Example 7. Media were prepared with increasing amount of soybean meal, from 25 g to 100 g per litre, and their ability to support protease overexpression were examined in shake flask. At 4 hours post-induction, all samples were collected and 10 μl supernatant was analyzed by SDS/PAGE (FIG. 6). The enzyme activities are shown in table 5.

| Media ingredients: | |
|---|---|
| Medium SBM | g/liter |
| Soybean Meal | 25–100 |
| CaCO₃ | 5 |
| Potato Starch | 5 |

TABLE 5

Enzyme activities of proteases BPN' expressed in various media.

| Proteases | Substrates | BHY | B2 | E1 | SBM25 g | SBM50 g | SBM100 g | CP |
|---|---|---|---|---|---|---|---|---|
| BPN' | sAAPF-pNA | 9.51 | 5.29 | 5.22 | 2.80 | 8.42 | 32.09 | 0.82 |

The enzyme activities are expressed in U/ml of culture supernatant. For CP, a protease powder concentrate (Savinase 4.0T), the enzyme unit is expressed in U/mg.

EQUIVALENTS

It will be appreciated that the various features described herein may be used singly or in any combination thereof. Therefore, the present invention is not limited to only the embodiments specifically described herein. While the foregoing description and drawings represent a preferred embodiment of the present invention, it will be understood that various additions, modifications, and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiment is therefore to be considered in all respects as illustrative and not restrictive, the scope of the invention being indicated by the appended claims, and not limited to the foregoing description.

What is claimed is:

1. A process for production of a protease comprising cultivating a recombinant *Bacillus* strain containing an expression vector comprising:
   a. a promoter region of the ORF19 of the bacteriophage phi-105 consisting of SEQ ID NO:14; and
   b. a DNA molecule, encoding the protease, wherein said molecule has over 95% homology to SEQ ID NO:7 or 9.

2. The process according to claim 1, wherein said DNA molecule is SEQ ID NO: 7 or 9.

3. The process according to claim 1, in which the promoter is induced by heat.

4. A process according to claim 1, further comprising the steps of separating or purifying the said protease.

5. A process for production of a protease comprising cultivating a recombinant *Bacillus* strain containing an expression vector comprising:
   a. a promoter region of the ORF19 of the bacteriophage phi-105 consisting of SEQ ID NO: 14; and
   b. a DNA molecule encoding the protease wherein said protease is from any prokaryotic or eukaryotic organism and wherein said DNA molecule has over 95% homology with SEQ ID NO: 7 or 9.

6. An expression vector comprising:
   a. a promoter region of the OFR19 of the bacteriophage phi-105 consisting of SEQ ID NO:14; and
   b. a nucleic acid molecule encoding an amino acid sequence of SEQ ID NO: 8 or 10.

* * * * *

SEQUENCE LISTING

<160> NUMBER OF SEQ ID NOS: 15

<210> SEQ ID NO 1
<211> LENGTH: 37
<212> TYPE: DNA
<213> ORGANISM: Artificial Sequence
<220> FEATURE:
<223> OTHER INFORMATION: Primer

<400> SEQUENCE: 1
gcgatcgcat atgagaagca aaaaattgtg gatcagc         37

<210> SEQ ID NO 2
<211> LENGTH: 33
<212> TYPE: DNA
<213> ORGANISM: Artificial Sequence
<220> FEATURE:
<223> OTHER INFORMATION: Primer

<400> SEQUENCE: 2
gcggatccgc ggccgcctgc gcagacatgt tgc         33

<210> SEQ ID NO 3
<211> LENGTH: 35
<212> TYPE: DNA
<213> ORGANISM: Artificial Sequence
<220> FEATURE:
<223> OTHER INFORMATION: Primer

<400> SEQUENCE: 3
gcgatatcgc ggccgcaggg aaatcaaacg gggaa         35

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
gcggatccac ttggccgtta cgggact         27

<210> SEQ ID NO 5
<211> LENGTH: 35
<212> TYPE: DNA
<213> ORGANISM: Artificial Sequence
<220> FEATURE:
<223> OTHER INFORMATION: Primer

<400> SEQUENCE: 5
gcgatatcgc ggccgctcaa ccggcgaaaa atgtt         35

<210> SEQ ID NO 6
<211> LENGTH: 29
<212> TYPE: DNA
<213> ORGANISM: Artificial Sequence
<220> FEATURE:
<223> OTHER INFORMATION: Primer

<400> SEQUENCE: 6
gcggatcctt attgagcggc agcttcgac         29

<210> SEQ ID NO 7
<211> LENGTH: 1149

```
<212> TYPE: DNA
<213> ORGANISM: Bacillus amyloliquifaciens

<400> SEQUENCE: 7
gtgagaggca aaaagtatg  gatcagtttg  ctgtttgctt  tagcgttaat  ctttacgatg     60
gcgttcggca gcacatcctc tgcccaggcg gcagggaaat  caaacgggga  aagaaatat     120
attgtcgggt ttaaacagac aatgagcacg atgagcgccg  ctaagaagaa  agatgtcatt    180
tctgaaaaag gcgggaaagt gcaaaagcaa ttcaaatatg  tagacgcagc  ttcagctaca    240
ttaaacgaaa aagctgtaaa agaattgaaa aaagacccga  gcgtcgctta  cgttgaagaa    300
gatcacgtag cacatgcgta cgcgcagtcc gtgccttacg  gcgtatcaca  aattaaagcc    360
cctgctctgc actctcaagg ctacactgga tcaaatgtta  aagtagcggt  tatcgacagc    420
ggtatcgatt cttctcatcc tgatttaaag gtagcaggcg  agccagcat   ggttccttct    480
gaaacaaatc ctttccaaga caacaactct cacggaactc  acgttgccgg  cacagttgcg    540
gctcttaata actcaatcgg tgtattaggc gttgcgccaa  gcgcatcact  ttacgctgta    600
aaagttctcg gtgctgacgg ttccggccaa tacagctgga  tcattaacgg  aatcgagtgg    660
gcgatcgcaa acaatatgga cgttattaac atgagcctcg  gcggaccttc  tggttctgct    720
gctttaaaag cggcagttga taaagccgtt gcatccggcg  tcgtagtcgt  tgcggcagcc    780
ggtaacgaag gcacttccgg cagctcaagc acagtgggct  accctggtaa  ataccttct    840
gtcattgcag taggcgctgt tgacagcagc aaccaaagag  catctttctc  aagcgtagga    900
cctgagcttg atgtcatggc acctggcgta tctatccaaa  gcacgcttcc  tggaaacaaa    960
tacgggcgt  acaacggtac gtcaatggca tctccgcacg  ttgccggagc  ggctgctttg    1020
attctttcta gcaccccgaa ctggacaaac actcaagtcc  gcagcagttt  agaaaacacc    1080
actacaaaac ttggtgattc tttctactat ggaaagggc   tgatcaacgt  acaggcggca    1140
gctcagtaa                                                              1149

<210> SEQ ID NO 8
<211> LENGTH: 382
<212> TYPE: PRT
<213> ORGANISM: Bacillus amyloliquifaciens

<400> SEQUENCE: 8

Val Arg Gly Lys Lys Val Trp Ile Ser Leu Leu Phe Ala Leu Ala Leu
  1               5                  10                  15

Ile Phe Thr Met Ala Phe Gly Ser Thr Ser Ser Ala Gln Ala Ala Gly
             20                  25                  30

Lys Ser Asn Gly Glu Lys Lys Tyr Ile Val Gly Phe Lys Gln Thr Met
         35                  40                  45

Ser Thr Met Ser Ala Ala Lys Lys Lys Asp Val Ile Ser Glu Lys Gly
     50                  55                  60

Gly Lys Val Gln Lys Gln Phe Lys Tyr Val Asp Ala Ala Ser Ala Thr
 65                  70                  75                  80

Leu Asn Glu Lys Ala Val Lys Glu Leu Lys Lys Asp Pro Ser Val Ala
                 85                  90                  95

Tyr Val Glu Glu Asp His Val Ala His Ala Tyr Ala Gln Ser Val Pro
            100                 105                 110

Tyr Gly Val Ser Gln Ile Lys Ala Pro Ala Leu His Ser Gln Gly Tyr
        115                 120                 125

Thr Gly Ser Asn Val Lys Val Ala Val Ile Asp Ser Gly Ile Asp Ser
    130                 135                 140
```

```
Ser His Pro Asp Leu Lys Val Ala Gly Gly Ala Ser Met Val Pro Ser
145                 150                 155                 160

Glu Thr Asn Pro Phe Gln Asp Asn Asn Ser His Gly Thr His Val Ala
                165                 170                 175

Gly Thr Val Ala Ala Leu Asn Asn Ser Ile Gly Val Leu Gly Val Ala
            180                 185                 190

Pro Ser Ala Ser Leu Tyr Ala Val Lys Val Leu Gly Ala Asp Gly Ser
        195                 200                 205

Gly Gln Tyr Ser Trp Ile Ile Asn Gly Ile Glu Trp Ala Ile Ala Asn
    210                 215                 220

Asn Met Asp Val Ile Asn Met Ser Leu Gly Gly Pro Ser Gly Ser Ala
225                 230                 235                 240

Ala Leu Lys Ala Ala Val Asp Lys Ala Val Ala Ser Gly Val Val Val
                245                 250                 255

Val Ala Ala Ala Gly Asn Glu Gly Thr Ser Gly Ser Ser Ser Thr Val
            260                 265                 270

Gly Tyr Pro Gly Lys Tyr Pro Ser Val Ile Ala Val Gly Ala Val Asp
        275                 280                 285

Ser Ser Asn Gln Arg Ala Ser Phe Ser Ser Val Gly Pro Glu Leu Asp
    290                 295                 300

Val Met Ala Pro Gly Val Ser Ile Gln Ser Thr Leu Pro Gly Asn Lys
305                 310                 315                 320

Tyr Gly Ala Tyr Asn Gly Thr Ser Met Ala Ser Pro His Val Ala Gly
                325                 330                 335

Ala Ala Ala Leu Ile Leu Ser Lys His Pro Asn Trp Thr Asn Thr Gln
            340                 345                 350

Val Arg Ser Ser Leu Glu Asn Thr Thr Thr Lys Leu Gly Asp Ser Phe
        355                 360                 365

Tyr Tyr Gly Lys Gly Leu Ile Asn Val Gln Ala Ala Ala Gln
    370                 375                 380

<210> SEQ ID NO 9
<211> LENGTH: 1140
<212> TYPE: DNA
<213> ORGANISM: Bacillus licheniformis

<400> SEQUENCE: 9
atgatgagga aaaagagttt ttggcttggg atgctgacgg ccttcatgct cgtgttcacg      60
atggcattca gcgattccgc ttctgctgct caaccggcga aaatgttga aaggattat      120 attgtcggat ttaagtcagg agtgaaaacc gcatctgtca aaaggacat catcaaagag      180 agcggcggaa aagtggacaa gcagtttaga atcatcaacg cggcaaaagc gaagctagac      240
aaagaagcgc ttaaggaagt caaaaatgat ccggatgtcg cttatgtgga agaggatcat      300
gtggcccatg ccttggcgca aaccgttcct tacggcattc tctcattaa agcggacaaa      360 gtgcaggctc aaggctttaa gggagcgaat gtaaaagtag ccgtcctgga tacaggaatc      420
caagcttctc atccggactt gaacgtagtc ggcggagcaa gctttgtggc tgcgaagct       480 tataacaccg acggcaacgg acacggcaca catgttgccg gtacagtagc tgcgcttgac      540
aatacaacgg gtgtattagg cgttgcgcca agcgtatcct tgtacgcggt taaagtactg      600
aattcaagcg gaagcggaac ttacagcggc attgtaagcg gaatcgagtg gcgacgaca       660 aacggcatgg atgttatcaa catgagtctt ggaggaccat caggctcaac agcgatgaaa      720
caggcggttg acaatgcata tgcaagaggg gttgtcgttg tggcggctgc tgggaacagc      780
```

-continued

```
ggatcttcag gaaacacgaa tacaatcggc tatcctgcga aatacgactc tgtcatcgca    840
gttggcgcgg tagactctaa cagcaacaga gcttcatttt ccagcgtcgg agcagagctt    900
gaagtcatgg ctcctggcgc aggcgtgtac agcacttacc caaccagcac ttatgcaaca    960
ttgaacggaa cgtcaatggc ttctcctcat gtagcgggag cagcagcttt gatcttgtca   1020
aaacatccga acctttcagc ttcacaagtc gcaaccgtc tctccagtac ggcgacttat    1080
ttgggaagct ccttctacta tggaaaaggt ctgatcaatg tcgaagctgc cgctcaataa   1140
```

<210> SEQ ID NO 10
<211> LENGTH: 379
<212> TYPE: PRT
<213> ORGANISM: Bacillus licheniformis

<400> SEQUENCE: 10

```
Met Met Arg Lys Lys Ser Phe Trp Leu Gly Met Leu Thr Ala Phe Met
 1               5                  10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Ile Ile Lys Glu Ser Gly Gly Lys
    50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
        115                 120                 125

Ala Asn Val Lys Val Ala Val Leu Asp Thr Gly Ile Gln Ala Ser His
    130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Ser Val
            180                 185                 190

Ser Leu Tyr Ala Val Lys Val Leu Asn Ser Ser Gly Ser Gly Thr Tyr
        195                 200                 205

Ser Gly Ile Val Ser Gly Ile Glu Trp Ala Thr Thr Asn Gly Met Asp
    210                 215                 220

Val Ile Asn Met Ser Leu Gly Gly Pro Ser Gly Ser Thr Ala Met Lys
225                 230                 235                 240

Gln Ala Val Asp Asn Ala Tyr Ala Arg Gly Val Val Val Ala Ala
                245                 250                 255

Ala Gly Asn Ser Gly Ser Ser Gly Asn Thr Asn Thr Ile Gly Tyr Pro
            260                 265                 270

Ala Lys Tyr Asp Ser Val Ile Ala Val Gly Ala Val Asp Ser Asn Ser
        275                 280                 285

Asn Arg Ala Ser Phe Ser Ser Val Gly Ala Glu Leu Glu Val Met Ala
    290                 295                 300

Pro Gly Ala Gly Val Tyr Ser Thr Tyr Pro Thr Ser Thr Tyr Ala Thr
```

```
                    305                 310                 315                 320
Leu Asn Gly Thr Ser Met Ala Ser Pro His Val Ala Gly Ala Ala Ala
                325                 330                 335
Leu Ile Leu Ser Lys His Pro Asn Leu Ser Ala Ser Gln Val Arg Asn
                340                 345                 350
Arg Leu Ser Ser Thr Ala Thr Tyr Leu Gly Ser Ser Phe Tyr Tyr Gly
            355                 360                 365
Lys Gly Leu Ile Asn Val Glu Ala Ala Ala Gln
        370                 375

<210> SEQ ID NO 11
<211> LENGTH: 382
<212> TYPE: PRT
<213> ORGANISM: Artificial Sequence
<220> FEATURE:
<223> OTHER INFORMATION: Fusion protein between the signal peptide from
      B. subtilis and BPN' protease from B. amyloliquifaciens

<400> SEQUENCE: 11

Met Arg Ser Lys Lys Leu Trp Ile Ser Leu Leu Phe Ala Leu Thr Leu
 1               5                  10                  15
Ile Phe Thr Met Ala Phe Ser Asn Met Ser Ala Gln Ala Ala Ala Gly
                20                  25                  30
Lys Ser Asn Gly Glu Lys Lys Tyr Ile Val Gly Phe Lys Gln Thr Met
            35                  40                  45
Ser Thr Met Ser Ala Ala Lys Lys Lys Asp Val Ile Ser Glu Lys Gly
        50                  55                  60
Gly Lys Val Gln Lys Gln Phe Lys Tyr Val Asp Ala Ala Ser Ala Thr
65                  70                  75                  80
Leu Asn Glu Lys Ala Val Lys Glu Leu Lys Lys Asp Pro Ser Val Ala
                85                  90                  95
Tyr Val Glu Glu Asp His Val Ala His Ala Tyr Ala Gln Ser Val Pro
            100                 105                 110
Tyr Gly Val Ser Gln Ile Lys Ala Pro Ala Leu His Ser Gln Gly Tyr
        115                 120                 125
Thr Gly Ser Asn Val Lys Val Ala Val Ile Asp Ser Gly Ile Asp Ser
    130                 135                 140
Ser His Pro Asp Leu Lys Val Ala Gly Gly Ala Ser Met Val Pro Ser
145                 150                 155                 160
Glu Thr Asn Pro Phe Gln Asp Asn Asn Ser His Gly Thr His Val Ala
                165                 170                 175
Gly Thr Val Ala Ala Leu Asn Asn Ser Ile Gly Val Leu Gly Val Ala
            180                 185                 190
Pro Ser Ala Ser Leu Tyr Ala Val Lys Val Leu Gly Ala Asp Gly Ser
        195                 200                 205
Gly Gln Tyr Ser Trp Ile Ile Asn Gly Ile Glu Trp Ala Ile Ala Asn
    210                 215                 220
Asn Met Asp Val Ile Asn Met Ser Leu Gly Gly Pro Ser Gly Ser Ala
225                 230                 235                 240
Ala Leu Lys Ala Ala Val Asp Lys Ala Val Ala Ser Gly Val Val Val
                245                 250                 255
Val Ala Ala Ala Gly Asn Glu Gly Thr Ser Gly Ser Ser Ser Thr Val
            260                 265                 270
Gly Tyr Pro Gly Lys Tyr Pro Ser Val Ile Ala Val Gly Ala Val Asp
        275                 280                 285
```

-continued

Ser Ser Asn Gln Arg Ala Ser Phe Ser Ser Val Gly Pro Glu Leu Asp
    290                 295                 300

Val Met Ala Pro Gly Val Ser Ile Gln Ser Thr Leu Pro Gly Asn Lys
305                 310                 315                 320

Tyr Gly Ala Tyr Asn Gly Thr Ser Met Ala Ser Pro His Val Ala Gly
                325                 330                 335

Ala Ala Ala Leu Ile Leu Ser Lys His Pro Asn Trp Thr Asn Thr Gln
            340                 345                 350

Val Arg Ser Ser Leu Glu Asn Thr Thr Thr Lys Leu Gly Asp Ser Phe
        355                 360                 365

Tyr Tyr Gly Lys Gly Leu Ile Asn Val Gln Ala Ala Gln
    370                 375                 380

<210> SEQ ID NO 12
<211> LENGTH: 380
<212> TYPE: PRT
<213> ORGANISM: Artificial Sequence
<220> FEATURE:
<223> OTHER INFORMATION: Fusion protein between the signal peptide from
      B. subtilis and Carlsberg protease from B.licheniformis

<400> SEQUENCE: 12

Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Ala Gln
            20                  25                  30

Pro Ala Lys Asn Val Glu Lys Asp Tyr Ile Val Gly Phe Lys Ser Gly
        35                  40                  45

Val Lys Thr Ala Ser Val Lys Lys Asp Ile Ile Lys Glu Ser Gly Gly
    50                  55                  60

Lys Val Asp Lys Gln Phe Arg Ile Ile Asn Ala Ala Lys Ala Lys Leu
65                  70                  75                  80

Asp Lys Glu Ala Leu Lys Glu Val Lys Asn Asp Pro Asp Val Ala Tyr
                85                  90                  95

Val Glu Glu Asp His Val Ala His Ala Leu Ala Gln Thr Val Pro Tyr
            100                 105                 110

Gly Ile Pro Leu Ile Lys Ala Asp Lys Val Gln Ala Gln Gly Phe Lys
        115                 120                 125

Gly Ala Asn Val Lys Val Ala Val Leu Asp Thr Gly Ile Gln Ala Ser
    130                 135                 140

His Pro Asp Leu Asn Val Val Gly Gly Ala Ser Phe Val Ala Gly Glu
145                 150                 155                 160

Ala Tyr Asn Thr Asp Gly Asn Gly His Gly Thr His Val Ala Gly Thr
                165                 170                 175

Val Ala Ala Leu Asp Asn Thr Thr Gly Val Leu Gly Val Ala Pro Ser
            180                 185                 190

Val Ser Leu Tyr Ala Val Lys Val Leu Asn Ser Ser Gly Ser Gly Thr
        195                 200                 205

Tyr Ser Gly Ile Val Ser Gly Ile Glu Trp Ala Thr Thr Asn Gly Met
    210                 215                 220

Asp Val Ile Asn Met Ser Leu Gly Gly Pro Ser Gly Ser Thr Ala Met
225                 230                 235                 240

Lys Gln Ala Val Asp Asn Ala Tyr Ala Arg Gly Val Val Val Val Ala
                245                 250                 255

Ala Ala Gly Asn Ser Gly Ser Ser Gly Asn Thr Asn Thr Ile Gly Tyr
            260                 265                 270

```
Pro Ala Lys Tyr Asp Ser Val Ile Ala Val Gly Ala Val Asp Ser Asn
            275                 280                 285

Ser Asn Arg Ala Ser Phe Ser Ser Val Gly Ala Glu Leu Glu Val Met
            290                 295                 300

Ala Pro Gly Ala Gly Val Tyr Ser Thr Tyr Pro Thr Ser Thr Tyr Ala
305                 310                 315                 320

Thr Leu Asn Gly Thr Ser Met Ala Ser Pro His Val Ala Gly Ala Ala
            325                 330                 335

Ala Leu Ile Leu Ser Lys His Pro Asn Leu Ser Ala Ser Gln Val Arg
            340                 345                 350

Asn Arg Leu Ser Ser Thr Ala Thr Tyr Leu Gly Ser Ser Phe Tyr Tyr
            355                 360                 365

Gly Lys Gly Leu Ile Asn Val Glu Ala Ala Ala Gln
            370                 375                 380

<210> SEQ ID NO 13
<211> LENGTH: 20
<212> TYPE: DNA
<213> ORGANISM: Artificial Sequence
<220> FEATURE:
<223> OTHER INFORMATION: phi-105 ORF 19 promoter-specific primer

<400> SEQUENCE: 13
atagacaatc ggcggttaac                                                 20

<210> SEQ ID NO 14
<211> LENGTH: 478
<212> TYPE: DNA
<213> ORGANISM: phi-105 bacteriophage
<220> FEATURE:
<223> OTHER INFORMATION: phi-105 ORF 19 promoter

<400> SEQUENCE: 14
tttattggaa ttaagagtct ctgggactgc tcttgtaaat gctccttgta atttaaagga      60
tattgacata acgaaatggt tgtgtaaaac agggagatta tatcttgata aggttaagaa    120
atttgaaata gttactattc tttcccatga cgtagaaaat caaaagatta taacagaatg    180
ggagtcactc cgcagagagg ctttacccga acaatttgat tcataagaac taattagtag    240
cgctttccaa tggaggcgct ttttatttg ggtagttgca taccactaaa gatgttcagg     300
tgcacatgag cattggagga aaggaacgct ttagggggga gggaaacctt taaacagtct    360
taatccccct tgattttatg ttctctgtaa actgcgtccg gtaaatctca ggatagacaa    420
tcggcggtta acggcttgag tgcgggggca gtttagaaag aatatgattg gagggatt     478

<210> SEQ ID NO 15
<211> LENGTH: 30
<212> TYPE: PRT
<213> ORGANISM: Bacillus subtilis
<220> FEATURE:
<223> OTHER INFORMATION: signal peptide from Bacillus subtilis

<400> SEQUENCE: 15

Met Arg Ser Lys Lys Leu Trp Ile Ser Leu Leu Phe Ala Leu Thr Leu
  1               5                  10                  15

Ile Phe Thr Met Ala Phe Ser Asn Met Ser Ala Gln Ala Ala
            20                  25                  30
```